United States Patent
Gaiser et al.

(10) Patent No.: US 6,547,776 B1
(45) Date of Patent: Apr. 15, 2003

(54) SYSTEMS AND METHODS FOR TREATING TISSUE IN THE CRURA

(75) Inventors: John Gaiser, Mountain View, CA (US); David Utley, San Carlos, CA (US)

(73) Assignee: Curon Medical, Inc., Sunnyvale, CA (US)

( * ) Notice: Subject to any disclaimer, the term of this patent is extended or adjusted under 35 U.S.C. 154(b) by 0 days.

(21) Appl. No.: 09/476,537

(22) Filed: Jan. 3, 2000

(51) Int. Cl.$^7$ .............................................. A61M 31/00
(52) U.S. Cl. ........................ 604/506; 604/21; 604/22; 604/514; 604/103.02; 606/41; 607/101; 607/105
(58) Field of Search ......................... 604/22, 21, 500, 604/506–509, 514, 516, 96.01, 103.02, 103.06, 19, 20; 606/41; 607/100–105

(56) References Cited

U.S. PATENT DOCUMENTS

| | | |
|---|---|---|
| 1,798,902 A | 3/1931 | Raney |
| 3,517,128 A | 6/1970 | Hines |
| 3,901,241 A | 8/1975 | Allen, Jr. |
| 4,011,872 A | 3/1977 | Komiya |
| 4,196,724 A | 4/1980 | Wirt et al. |
| 4,411,266 A | 10/1983 | Cosman |
| 4,423,812 A | 1/1984 | Sato |
| 4,532,924 A | 8/1985 | Auth et al. |
| 4,565,200 A | 1/1986 | Cosman |
| 4,705,041 A | 11/1987 | Kim |
| 4,901,737 A | 2/1990 | Toone |
| 4,906,203 A | 3/1990 | Margrave et al. |
| 4,907,589 A | 3/1990 | Cosman |
| 4,943,290 A | 7/1990 | Rexroth et al. |
| 4,947,842 A | 8/1990 | Marchosky et al. |
| 4,955,377 A | 9/1990 | Lennox et al. |
| 4,966,597 A | 10/1990 | Cosman |
| 4,976,711 A | 12/1990 | Parins et al. |
| 5,019,075 A | 5/1991 | Spears et al. |
| 5,035,696 A | 7/1991 | Rydell |
| 5,046,512 A | 9/1991 | Murchie |
| 5,047,028 A | 9/1991 | Qian |
| 5,057,107 A | 10/1991 | Parins et al. |
| 5,078,717 A | 1/1992 | Parins et al. |
| 5,083,565 A | 1/1992 | Parins |

(List continued on next page.)

FOREIGN PATENT DOCUMENTS

| | | |
|---|---|---|
| DE | 43 03 882 | 2/1995 |
| DE | 38 38 840 | 2/1997 |
| EP | 0 139 607 | 5/1985 |

(List continued on next page.)

OTHER PUBLICATIONS

Woodward E R et al, Comparison of Crural Repair and Nissen Fundoplication in the Treatment of Esophageal Hiatus Hernia with Peptic Esophagitis, Annals of Surgery, May 1971, 173 (5), p. 782–792.*

(List continued on next page.)

*Primary Examiner*—Brian L. Casler
*Assistant Examiner*—Jeremy Thissell
(74) *Attorney, Agent, or Firm*—Ryan, Kromholz & Manion, SC

(57) ABSTRACT

Tissue in the crura is treated by advancing a tissue penetrating element from a catheter tube through a wall of the esophagus. The tissue penetrating element is operated to affect a tightening of the crura, e.g., to treat hiatal hernia.

7 Claims, 14 Drawing Sheets

U.S. PATENT DOCUMENTS

| | | |
|---|---|---|
| 5,084,044 A | 1/1992 | Quint |
| 5,088,979 A | 2/1992 | Filipi et al. |
| 5,094,233 A | 3/1992 | Brennan |
| 5,100,423 A | 3/1992 | Fearnot |
| 5,106,360 A | 4/1992 | Ishiwara et al. |
| 5,122,137 A | 6/1992 | Lennox |
| 5,125,928 A | 6/1992 | Parins et al. |
| 5,156,151 A | 10/1992 | Imran |
| 5,190,541 A | 3/1993 | Abele et al. |
| 5,197,963 A | 3/1993 | Parins |
| 5,197,964 A | 3/1993 | Parins |
| 5,205,287 A | 4/1993 | Erbel et al. |
| 5,215,103 A | 6/1993 | Desai |
| 5,232,444 A | 8/1993 | Just et al. |
| 5,236,413 A | 8/1993 | Fiering |
| 5,242,441 A | 9/1993 | Avitall |
| 5,254,126 A | 10/1993 | Filipi et al. |
| 5,256,138 A | 10/1993 | Vurek et al. |
| 5,257,451 A | 11/1993 | Edwards et al. |
| 5,263,493 A | 11/1993 | Avitall |
| 5,275,162 A | 1/1994 | Edwards et al. |
| 5,275,608 A | 1/1994 | Forman et al. |
| 5,275,610 A | 1/1994 | Eberbach |
| 5,277,201 A | 1/1994 | Stern |
| 5,281,216 A | 1/1994 | Klicek |
| 5,281,217 A | 1/1994 | Edwards et al. |
| 5,281,218 A | 1/1994 | Imran |
| 5,290,286 A | 3/1994 | Parins |
| 5,292,321 A | 3/1994 | Lee |
| 5,293,869 A | 3/1994 | Edwards et al. |
| 5,309,910 A | 5/1994 | Edwards et al. |
| 5,313,943 A | 5/1994 | Houser et al. |
| 5,314,466 A | 5/1994 | Stern et al. |
| 5,316,020 A | 5/1994 | Truffer |
| 5,324,284 A | 6/1994 | Imran |
| 5,328,467 A | 7/1994 | Edwards et al. |
| 5,334,196 A | 8/1994 | Scott et al. |
| 5,336,222 A | 8/1994 | Durgin, Jr. et al. |
| 5,345,936 A | 9/1994 | Pomeranz et al. |
| 5,348,554 A | 9/1994 | Imran et al. |
| 5,363,861 A | 11/1994 | Edwards et al. |
| 5,365,926 A | 11/1994 | Desai |
| 5,365,945 A | 11/1994 | Halstrom |
| 5,366,490 A | 11/1994 | Edwards et al. |
| 5,368,557 A | 11/1994 | Nita et al. |
| 5,368,592 A | 11/1994 | Stern et al. |
| 5,370,675 A | 12/1994 | Edwards et al. |
| 5,370,678 A | 12/1994 | Edwards et al. |
| 5,383,876 A | 1/1995 | Nardella |
| 5,383,917 A | 1/1995 | Desai et al. |
| 5,385,544 A | 1/1995 | Edwards et al. |
| 5,397,339 A | 3/1995 | Desai |
| 5,398,683 A | 3/1995 | Edwards et al. |
| 5,401,272 A | 3/1995 | Perkins |
| 5,403,311 A | 4/1995 | Abele et al. |
| 5,409,453 A | 4/1995 | Lundquist et al. |
| 5,409,483 A | 4/1995 | Campbell et al. |
| 5,415,657 A | 5/1995 | Taymor-Luia |
| 5,421,819 A | 6/1995 | Edwards et al. |
| 5,423,808 A | 6/1995 | Edwards et al. |
| 5,423,811 A | 6/1995 | Ellman et al. |
| 5,423,812 A | 6/1995 | Ellman et al. |
| 5,433,739 A | 7/1995 | Sluijter et al. |
| 5,435,805 A | 7/1995 | Edwards |
| 5,441,499 A | 8/1995 | Fritzsch |
| 5,443,470 A | 8/1995 | Stern et al. |
| 5,454,782 A | 10/1995 | Perkins |
| 5,456,662 A | 10/1995 | Edwards et al. |
| 5,456,682 A | 10/1995 | Edwards et al. |
| 5,458,596 A | 10/1995 | Lax et al. |
| 5,458,597 A | 10/1995 | Edwards et al. |
| 5,465,717 A | 11/1995 | Imran et al. |
| 5,470,308 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,490,984 A | 2/1996 | Freed |
| 5,496,271 A | 3/1996 | Burton et al. |
| 5,496,311 A | 3/1996 | Abele et al. |
| 5,500,012 A | 3/1996 | Brucker et al. |
| 5,505,728 A | 4/1996 | Ellman et al. |
| 5,505,730 A | 4/1996 | Edwards |
| 5,507,743 A | 4/1996 | Edwards et al. |
| 5,507,802 A * | 4/1996 | Imran |
| 5,509,419 A | 4/1996 | Edwards et al. |
| 5,514,130 A | 5/1996 | Baker |
| 5,514,131 A | 5/1996 | Edwards et al. |
| 5,520,684 A | 5/1996 | Imran |
| 5,531,676 A | 7/1996 | Edwards et al. |
| 5,531,677 A | 7/1996 | Lundquist et al. |
| 5,536,240 A | 7/1996 | Edwards et al. |
| 5,536,267 A | 7/1996 | Edwards et al. |
| 5,540,655 A | 7/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,562,720 A | 10/1996 | Stern et al. |
| 5,571,116 A | 11/1996 | Bolanos et al. |
| 5,578,007 A | 11/1996 | Imran |
| 5,588,432 A | 12/1996 | Crowley |
| 5,588,960 A | 12/1996 | Edwards et al. |
| 5,599,345 A | 2/1997 | Edwards et al. |
| 5,609,151 A | 3/1997 | Mulier et al. |
| 5,624,439 A | 4/1997 | Edwards et al. |
| 5,672,153 A | 9/1997 | Lax et al. |
| 5,676,674 A | 10/1997 | Bolanos et al. |
| 5,688,266 A | 11/1997 | Edwards et al. |
| 5,688,490 A | 11/1997 | Tournier et al. |
| 5,702,438 A | 12/1997 | Avitall |
| 5,709,224 A | 1/1998 | Behl et al. |
| 5,732,698 A | 3/1998 | Swanson et al. |
| 5,738,096 A | 4/1998 | Ben-Haim |
| 5,830,213 A | 11/1998 | Panescu et al. |
| 5,836,874 A | 11/1998 | Swanson et al. |
| 5,860,974 A | 1/1999 | Abele |
| 5,871,483 A | 2/1999 | Jackson et al. |
| 6,073,052 A | 6/2000 | Zelickson et al. |
| 6,323,037 B1 * | 11/2001 | Lauto et al. ................ 424/426 |
| 6,335,028 B1 * | 1/2002 | Vogel et al. ................ 424/1.11 |

FOREIGN PATENT DOCUMENTS

| | | |
|---|---|---|
| EP | 0 608 609 | 8/1994 |
| WO | 91/01773 | 2/1991 |
| WO | 92/10142 | 6/1992 |
| WO | 93/08755 | 5/1993 |
| WO | 94/10925 | 5/1994 |
| WO | 94/21165 | 9/1994 |
| WO | 94/21178 | 9/1994 |
| WO | 94/22366 | 10/1994 |
| WO | 94/26178 | 11/1994 |
| WO | 95/18575 | 7/1995 |
| WO | 95/19142 | 7/1995 |
| WO | 95/25472 | 9/1995 |
| WO | 96/00042 | 1/1996 |
| WO | 96/16606 | 6/1996 |
| WO | 96/29946 | 10/1996 |
| WO | 97/06857 | 2/1997 |
| WO | 97/32532 | 9/1997 |

WO 97/43971 11/1997

OTHER PUBLICATIONS

Castell, D.O. "Gastroesophageal Reflux Disease: Current Strategies for Patient Management." Arch Fam Med. 5(4): 221–7.

Dallemagne, B. et al., "Laparoscopic Nissen Fundoplication: Preliminary." Surgical Laparoscopy & Endoscopy. 1991 1(3): 138–43.

Hinder, R.A. et al., "The Technique of Laparoscopic Nissen Fundoplication." Surgical Laparoscopy & Endoscopy. 1992. 2(3): 265–272.

Karlstrom, L.H. et al. "Ectopic jejunal pacemakers and enterogastric reflux after Roux gastrectomy: Effect of intestinal pacing." Surgery 1989. 106(3): 486–495.

Kelly, KA. et al., "Doudenal–gastric reflux and slowed gastric emptying by electrical pacing of the canine doudenal pacesetter potential." Gastroenterology. 1977. 72(3): 429–33.

Reynolds, J.C. "Influence of pathophysiology, severity, and cost on the medical management of gastroesophageal reflux disease." Am J Health–Syst Pharm. 53 (22 Suppl 3): S5–12.

Urschel, J.D. "Complications of Antireflux Surgery." Am J Surg. 1993. 166(1): 68–70.

Kaneko, et al., Physiological Laryngeal Pacemaker, May 1985, Trans Am Soc. Artif. Intern Organs, vol. XXXI, pp. 293–296.

Mugica et al. Direct Diaphragm Stimulation, Jan. 1987 PACE, vol. 10, pp. 252–256.

Mugica et al., Neurostimulation: An Overview, Chapter 21, Preliminary Test of a Muscular Diaphragm pacing System on Human Patients. 1985. pp. 3. 263–279.

Rice et al., Endoscopic Paranasal Sinus Surgery, Chapter 5, Functional Endoscopic Paranasal Sinus Surgery, The Technique of Messerklinger, Raven Press, 1988, pp. 75–104.

Rice et al., Endoscopic Paranasal Sinus Surgery, Chapter 6, Total Endoscopic Sphenoethmoidectomy, The Technique of Wigand, Raven Press, 1988, pp. 105–125.

* cited by examiner

SYSTEMS AND METHODS FOR TREATING TISSUE IN THE CRURA

FIELD OF THE INVENTION

In a general sense, the invention is directed to systems and methods for treating interior tissue regions of the body. More specifically, the invention is directed to systems and methods for treating dysfunction in and around the lower esophageal sphincter and cardia of the stomach, and, in particular, hernias of the stomach through the esophageal hiatus and diaphragm, commonly called hiatal hernias.

BACKGROUND OF THE INVENTION

A. The Gastrointestinal Tract

The gastrointestinal tract, also called the alimentary canal, is a long tube through which food is taken into the body and digested. The alimentary canal begins at the mouth, and includes the pharynx, esophagus, stomach, small and large intestines, and rectum. In human beings, this passage is about 30 feet (9 meters) long.

Small, ring-like muscles, called sphincters, surround portions of the alimentary canal. In a healthy person, these muscles contract or tighten in a coordinated fashion during eating and the ensuing digestive process, to temporarily close off one region of the alimentary canal from an other.

For example, a muscular ring called the lower esophageal sphincter (or, in shorthand, LES) surrounds the junction of the esophagus and the stomach. The lower esophageal sphincter is a ring of increased thickness in the circular, smooth-muscle layer of the esophagus. Normally, the lower esophageal sphincter maintains a high-pressure zone between fifteen and thirty mm Hg above intragastric pressures inside the stomach.

The stomach muscles churn the food and digestive juices into a mass called chyme. Then the muscles squeeze the chyme toward the pyloric (intestinal) end of the stomach by peristaltic waves, which start at the top of the stomach and move downward. The pyloric sphincter, another ringlike muscle, surrounds the duodenal opening. The pyloric sphincter keeps food in the stomach until it is a liquid. The pyloric sphincter then relaxes and lets some chyme pass into the duodenum.

When a person swallows food, muscles of the pharynx push the food into the esophagus. The muscles in the esophagus walls respond with a wavelike contraction called peristalsis. The lower esophageal sphincter relaxes before the esophagus contracts, and allows food to pass through to the stomach. After food passes into the stomach, the lower esophageal sphincter constricts to prevent the contents from regurgitating into the esophagus.

B. Gastrointestinal Tract Sphincter Dysfunction

Dysfunction of a sphincter in the body can lead to internal damage or disease, discomfort, or otherwise adversely affect the quality of life. For example, if the lower esophageal sphincter fails to function properly, stomach acid may rise back into the esophagus. Unlike the stomach, the esophagus has no natural protection against stomach acids. When the stomach contents make contact with the esophagus, heartburn or other disease symptoms, including damage to the esophagus, can occur.

Gastrointestinal reflux disease (GERD) is a common disorder, characterized by spontaneous relaxation of the lower esophageal sphincter. It has been estimated that approximately two percent of the adult population suffers from GERD. The incidence of GERD increases markedly after the age of 40, and it is not uncommon for patients experiencing symptoms to wait years before seeking medical treatment.

GERD is believed to be caused by a combination of conditions that increase the presence of acid reflux in the esophagus. These conditions include transient LES relaxation, decreased LES resting tone, impaired esophageal clearance, delayed gastric emptying, decreased salivation, and impaired tissue resistance. Because the resting tone of the lower esophageal sphincter is maintained by both myogenic (muscular) and neurogenic (nerve) mechanisms, some believe that aberrant electrical signals in the lower esophageal sphincter or surrounding region of the stomach (called the cardia) can cause the sphincter to spontaneously relax.

Lifestyle factors can also cause increased risk of reflux. Smoking, large meals, fatty foods, caffeine, pregnancy, obesity, body position, drugs, hormones, and paraplegia may all exacerbate GERD.

The excessive reflux experienced by patients with GERD overwhelms their intrinsic mucosal defense mechanisms, resulting in many symptoms. The most common symptom of GERD is heartburn. Besides the discomfort of heartburn, reflux results in symptoms of esophageal inflammation, such as odynophagia (pain on swallowing) and dysphagia (difficult swallowing). The acid reflux may also cause pulmonary symptoms such as coughing, wheezing, asthma, aspiration pneumonia, and interstitial fibrosis; oral symptoms such as tooth enamel decay, gingivitis, halitosis, and waterbrash; throat symptoms such as a soreness, laryngitis, hoarseness, and a globus sensation; and earache.

Complications of GERD include esophageal erosion, esophageal ulcer, and esophageal stricture; replacement of normal esophageal epithelium with abnormal (Barrett's) epithelium; and pulmonary aspiration.

C. Other Dysfunction (Hiatal Hernia)

Normally, the diaphragm wraps about the LES, forming between it and the LES an aperture called the esophageal hiatus. Below the diaphragm, and still within the esophageal hiatus, two tendonous and muscular structures, referred to commonly as left and right crura also surround the LES.

The right crura and the left crura connect to the spine, generally at the second and fourth upper lumbar vertebra. The crura pass forward and inward and eventually diverge so as to surround the esophagus and LES.

A hiatal hernia develops when the entire LES moves upward away from the crura. The LES and part of the upper stomach push upward through the esophageal hiatus, and protrude above the diaphragm into the chest cavity.

A hiatal hernia may occur if the crura become weakened, or if a weakened region of the crura is accompanied with coughing, vomiting, straining during bowel movements, sudden exertion, pregnancy, or obesity. Occasionally, a hiatal hernia becomes large enough to allow as much as one-third or more of the stomach to protrude through the diaphragm. This can exert pressure on the lungs or diaphragm, making it difficult to breathe normally.

Hiatal hernia frequently accompanies severe GERD. The hernia may increase transient LES relaxation and delay acid clearance due to impaired esophageal emptying. Thus, hiatal hernias may contribute to prolonged acid exposure time following reflux, resulting in GERD symptoms and esophageal damage.

The herniated or enlarged portion of the stomach cavity can serve as a reservoir to collect refluxed stomach acid, and provide a readily available source of acid into the esophagus, thus intensifying the negative effects of gastrointestinal reflux disease (GERD). It is estimated that as many as 25%–50% of people older than 50 years suffer from hiatal hernias, although hiatal hernias may afflict sufferers at any age.

Hiatal hernias are often accompanied by painful burning sensations in the chest region, and the pain often intensifies on a full stomach or during pregnancy. Additionally, hiatal hernias are known to aggravate heartburn, and exert pressure on the lungs or diaphragm, causing breathing and swallowing difficulties.

In severe cases, hiatal hernias can create friction that cause lesions within the stomach. The lesions can bleed and lead to iron-deficiency anemia from chronic loss of blood. In the most severe cases, a large percentage of the stomach could protrude into the chest cavity, causing restricted blood flow to the stomach.

Hiatal hernias are presently treated with a variety of approaches. In less severe cases, no treatment may be necessary. Increasing in severity, lifestyle changes including dietary changes and quitting smoking may lessen the painful effects of a hiatal hernia.

With moderate cases, antacids are used to neutralize the stomach acid and reduce inflammation. Pepcid, Reglan, and Brevital are some common medicines, trade names for famotidine, metoclopramide, and methohexital, respectively.

In moderate to dangerously severe cases, invasive abdominal surgical intervention may be required to move the LES and crura into proper orientation with the diaphragm. The traditional method is an invasive surgery whereby an incision is made through the abdominal wall. The bulging tissue is returned to the abdominal cavity. The crura are re-approximated, and the fundus of the stomach is wrapped around the LES, thus securing the stomach in the proper intra-abdominal position. No implant is used for this repair.

Although these methods can capably treat hiatal hernias in certain instances, all surgical intervention entails making an incision into the abdomen and carry with it the usual risks of abdominal surgery.

SUMMARY OF THE INVENTION

One aspect of the invention provides systems and methods for treating tissue in the crura. The systems and methods introduce a catheter tube into a region of the esophagus adjoining the crura. The systems and methods advance a tissue penetrating element from the catheter tube through a wall of the esophagus and into contact with tissue in one or more crura. The tissue penetrating element is operated, e.g., to affect a tightening of the crura.

The tissue penetrating element can be operated in various ways to achieve this result. For example, the tissue penetration element can ablate the contacted tissue, e.g., by use of an ablating agent or by the application of energy (such as radio frequency energy) to the contacted tissue to form a lesion. Alternatively, the tissue penetrating element can staple or suture the contacted tissue to tighten the crura. Still alternatively, the tissue penetrating element can deliver an agent to the contacted tissue to affect tightening, e.g., a tissue bulking agent, a tissue growth factor, fibrosis inducer, fibroblast growth factor, or scerosant.

Another aspect of the invention provides systems and methods for treating hiatal hernia. The systems and methods locate the stomach in a proper intra-abdominal position below the diaphragm, and introduce a catheter tube into a region of the esophagus adjoining the crura. The systems and methods advance a tissue penetrating element from the catheter tube through a wall of the esophagus and into contact with tissue in one or more crura. The systems and methods tighten the one or more crura using the tissue penetrating element, to thereby retain the stomach in the proper intra-abdominal position.

Features and advantages of the inventions are set forth in the following Description and Drawings, as well as in the appended Claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

The Specification discloses various catheter-based systems and methods for treating or repairing a hiatal hernia by tightening the crura to retain the stomach below the diaphragm. The systems and methods can treat a hiatal hernia alone or in association with the treatment of dysfunction of the lower esophageal sphincter, such as GERD.

The systems and methods are particularly well suited for treating dysfunctions in and around the upper gastrointestinal tract, e.g., in the crura, lower esophageal sphincter, and adjacent cardia of the stomach. For this reason, the systems and methods will be described in this context.

Still, it should be appreciated that the disclosed systems and methods are applicable for use in treating other dysfunctions elsewhere in the body, which are not necessarily sphincter-related. For example, the various aspects of the invention have application in procedures requiring treatment of hemorrhoids, or incontinence, or restoring compliance to or otherwise tightening interior tissue or muscle regions. The systems and methods that embody features of the invention are also adaptable for use with systems and surgical techniques that are not necessarily catheter-based.

I. Anatomy of the Lower Esophageal Sphincter Region

Figure 1:
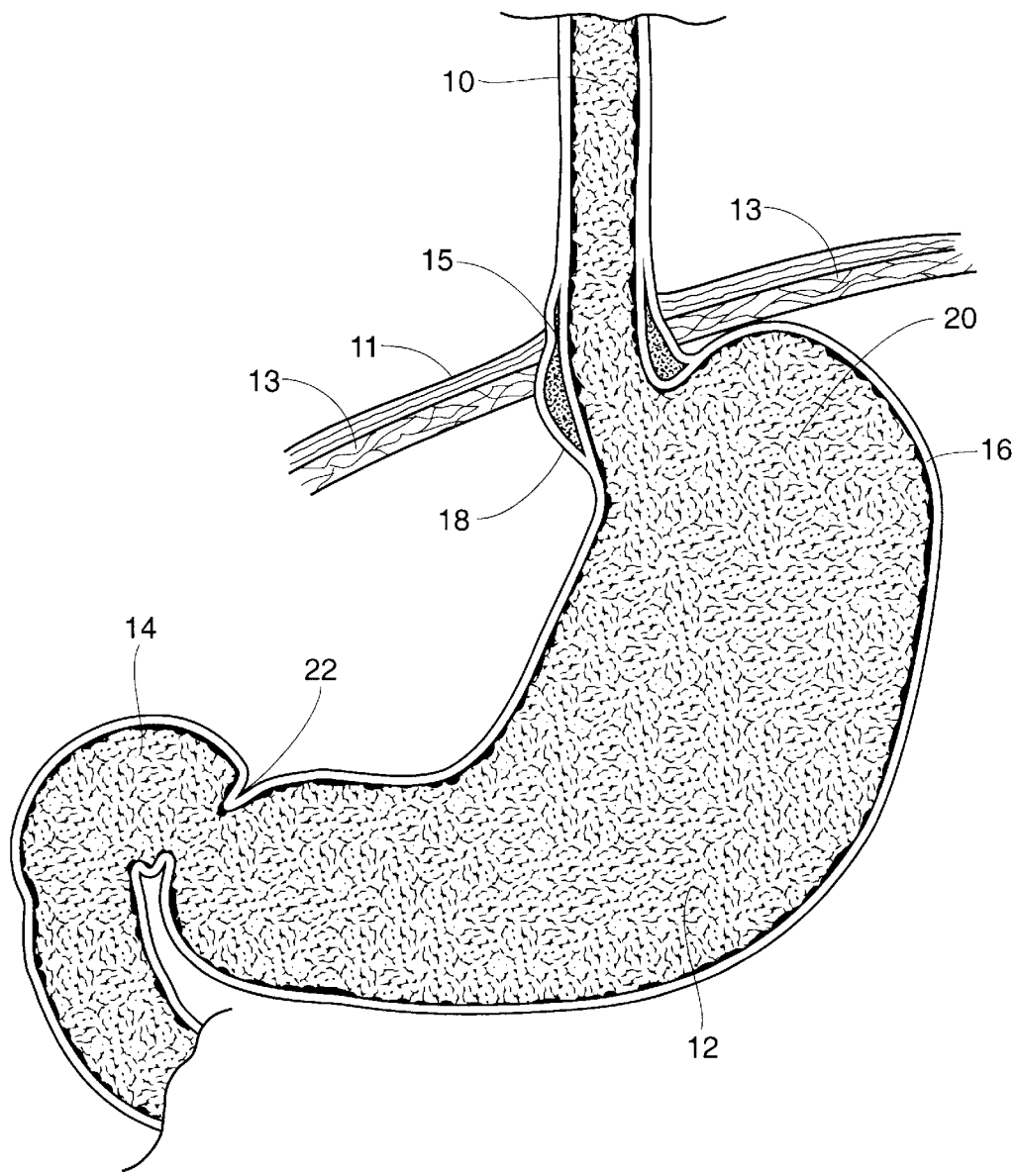
FIG. 1 is an anatomic view of the esophagus and stomach.

As FIG. 1 shows, the esophagus 10 is a muscular tube that carries food from the mouth past the diaphragm 11 to the stomach 12. The muscles in the walls of the esophagus 10 contract in a wavelike manner, moving the food down to the stomach 12. The interior wall of the esophagus includes glands that secrete mucus, to aid in the movement of food by providing lubrication. The human esophagus is about twenty-five centimeters long.

The stomach 12, located in the upper left hand side of the abdomen, lays between the esophagus 10 and the small intestine 14. In people and most animals, the stomach 12 is a simple baglike organ. A human being's stomach is shaped much like a J.

The average adult stomach can hold a little over one quart (0.95 liter). The stomach 12 serves as a storage place for food. Food in the stomach 12 is discharged slowly into the intestines 14. The stomach 12 also helps digest food.

The upper end of the stomach connects with the esophagus 10 at the cardiac notch 16, at the top of the J-shape. The muscular ring called the lower esophageal sphincter 18 surrounds the opening between the esophagus 10 and the stomach 12. The funnel-shaped region of the stomach 12 immediately adjacent to the sphincter 18 is called the cardia 20. The cardia 20 comprises smooth muscle. It is not a sphincter.

Figure 1A:
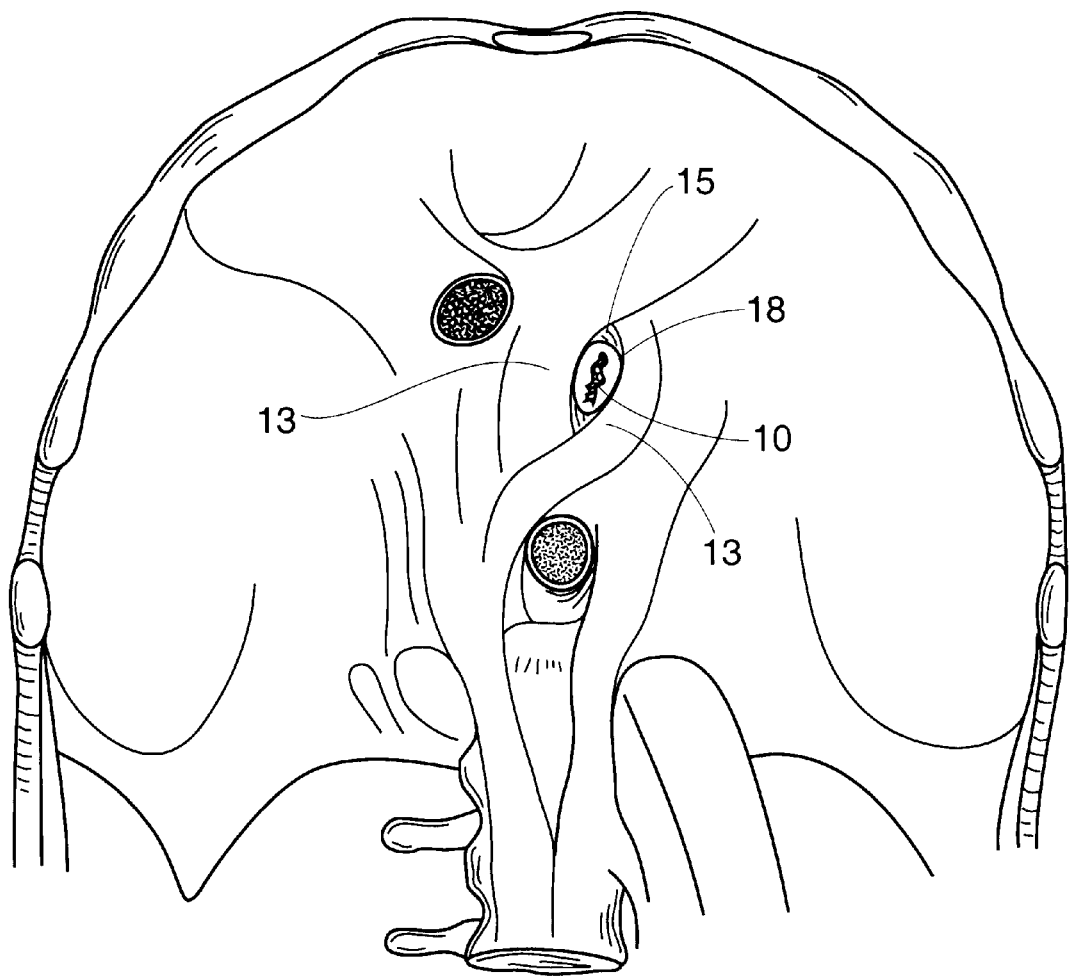
FIG. 1A is an anatomic view of the under surface of the diaphragm, showing the esophageal opening or esophageal hiatus in cross section, and the left and right crura in relation to the esophageal opening and lower esophageal sphincter.
Figure 1B:
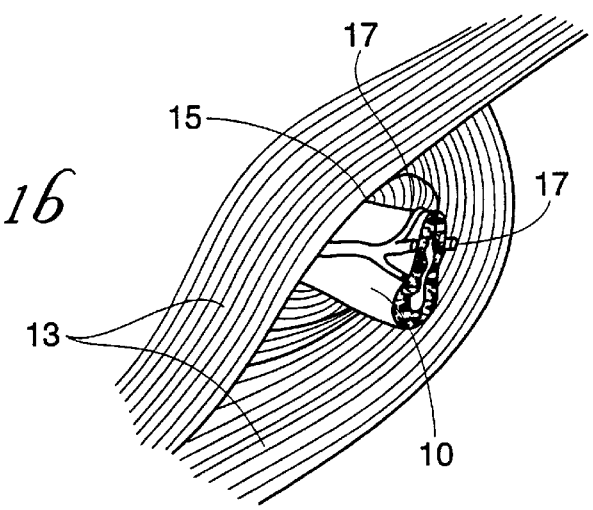
FIG. 1B is an anatomic inferior view of the abdominal surface of the diaphragm, showing the anterior and posterior vagal trunks, the esophageal hiatus, and the left and right crura.

Shown in FIGS. 1, 1A, and 1B, the esophageal hiatus 15, is an opening or void that surrounds the junction of the esophagus 10 and the stomach 12. In the hiatus 15, the esophagus 10 passes, in sequence, through the diaphragm 11, and then the left and right crura 13.

Anterior and posterior vagal nerves 17 (see FIGS. 1B and 1D) are located on the outer wall of the esophagus 10. The vagal nerves 17 are part of the esophageal branches of the glosso-pharyngeal pneumogastric. These nerves supply the vocal organs with motor and sensory fibers, and supply the pharynx, esophagus, stomach, and heart with motor fibers. These nerves 17, too, pass through the esophageal hiatus 15. FIG. 1E also shows the relative location of the anterior and posterior vagal nerves 17, esophageal arteries and veins 19, and lower esophageal sphincter 18 are shown.

Referring now to FIG. 1, the lower esophageal sphincter 18 relaxes, or opens, to allow swallowed food to enter the stomach 12. The lower esophageal sphincter 18, however, is normally closed, to keep the stomach 12 contents from flowing back into the esophagus 10.

Another sphincter, called the pyloric sphincter 22, surrounds the duodenal opening of the stomach 12. The pyloric sphincter 22 keeps non-liquid food material in the stomach 12 until it is processed into a more flowable, liquid form. The time that the stomach 12 retains food varies. Usually, the stomach 12 empties in three to five hours.

In a person suffering from GERD, the lower esophageal sphincter 18 is subject to spontaneous relaxation. The sphincter 18 opens independent of the normal swallowing function. Acidic stomach contents surge upward into the esophagus 10, causing pain, discomfort, and damage the mucosal wall of the esophagus 10.

The stomach 12 distends to accommodate various food volumes. Over time, stomach distention can stretch the cardia 20 or otherwise cause loss of compliance in the cardia 20. Loss of compliance in the cardia 20 can also pull the lower esophageal sphincter 18 open when the stomach 12 is distended, even absent sphincter muscle relaxation. The same undesired results occur: acidic stomach contents can surge upward into the esophagus 10 with the attendant undesired consequences.

Figure 1C:
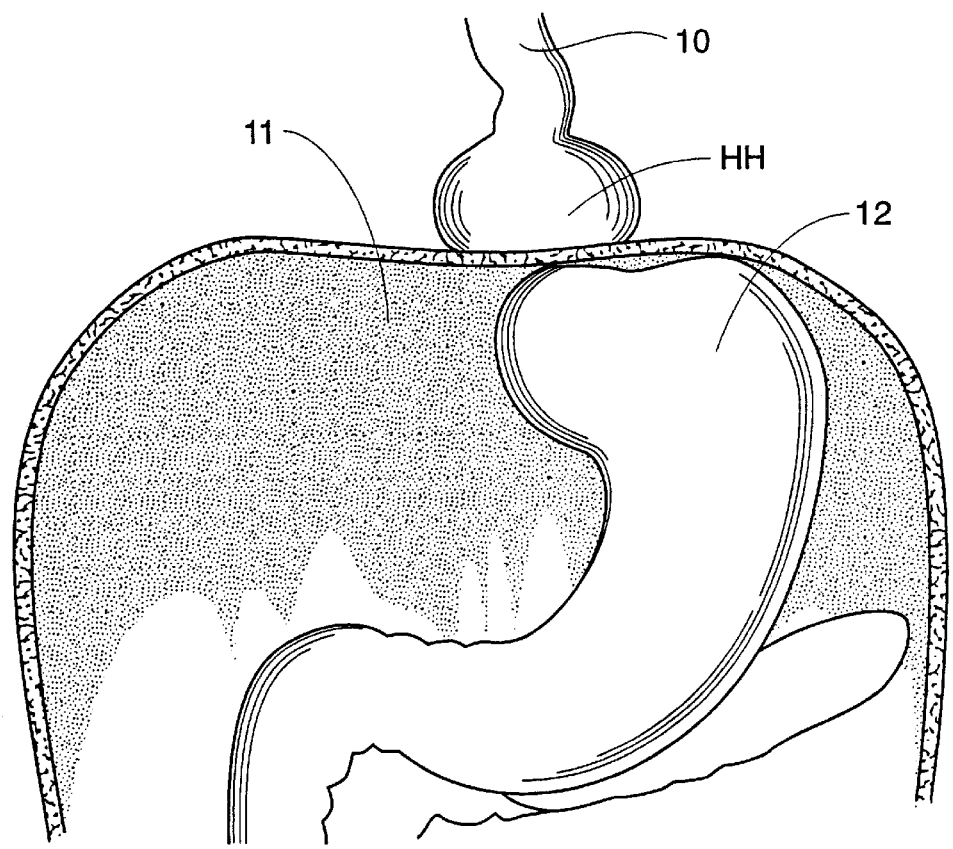
FIG. 1C is a illustrative view of a hiatal hernia showing a portion of a stomach penetrating through the diaphragm.
Figure 1D:
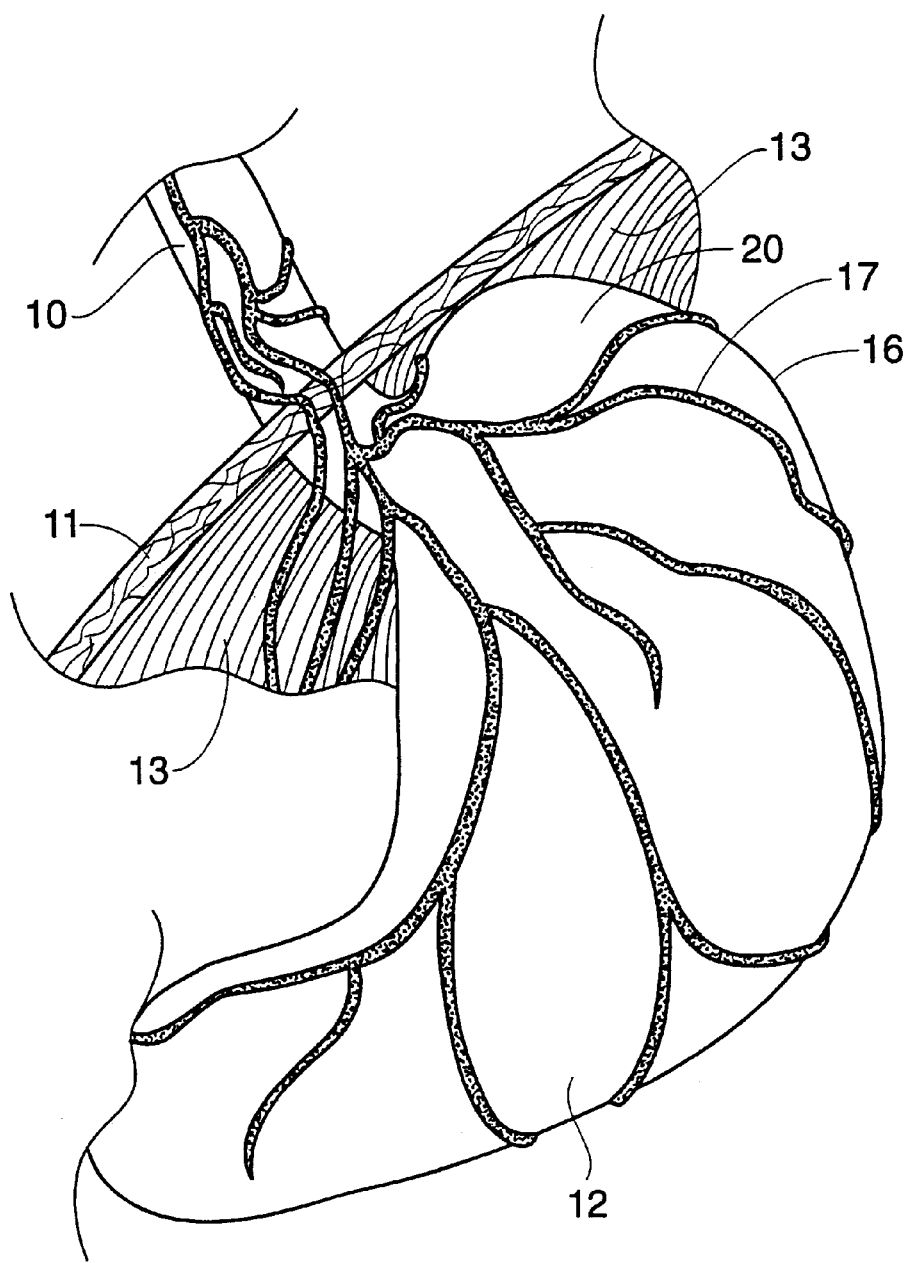
FIG. 1D is an anatomic view of the stomach, showing the location of the anterior and posterior vagal trunks in relation to the esophagus and the stomach.
Figure 1E:
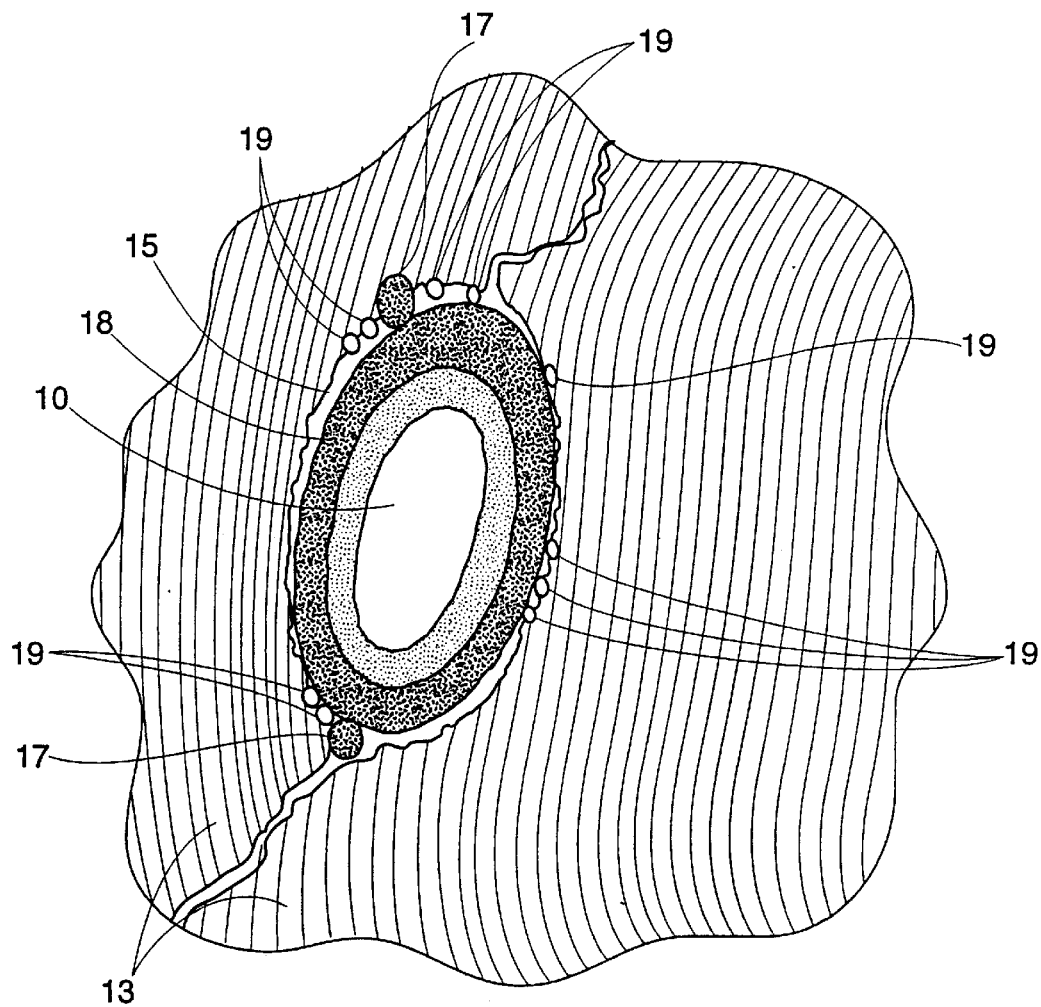
FIG. 1E shows an anterior cross-sectional view of a portion of the posterior abdominal wall, showing the location of the anterior and posterior vagal nerves in relation to the crura and lower esophageal sphincter, as well as esophageal arteries and veins.
Figure 9:
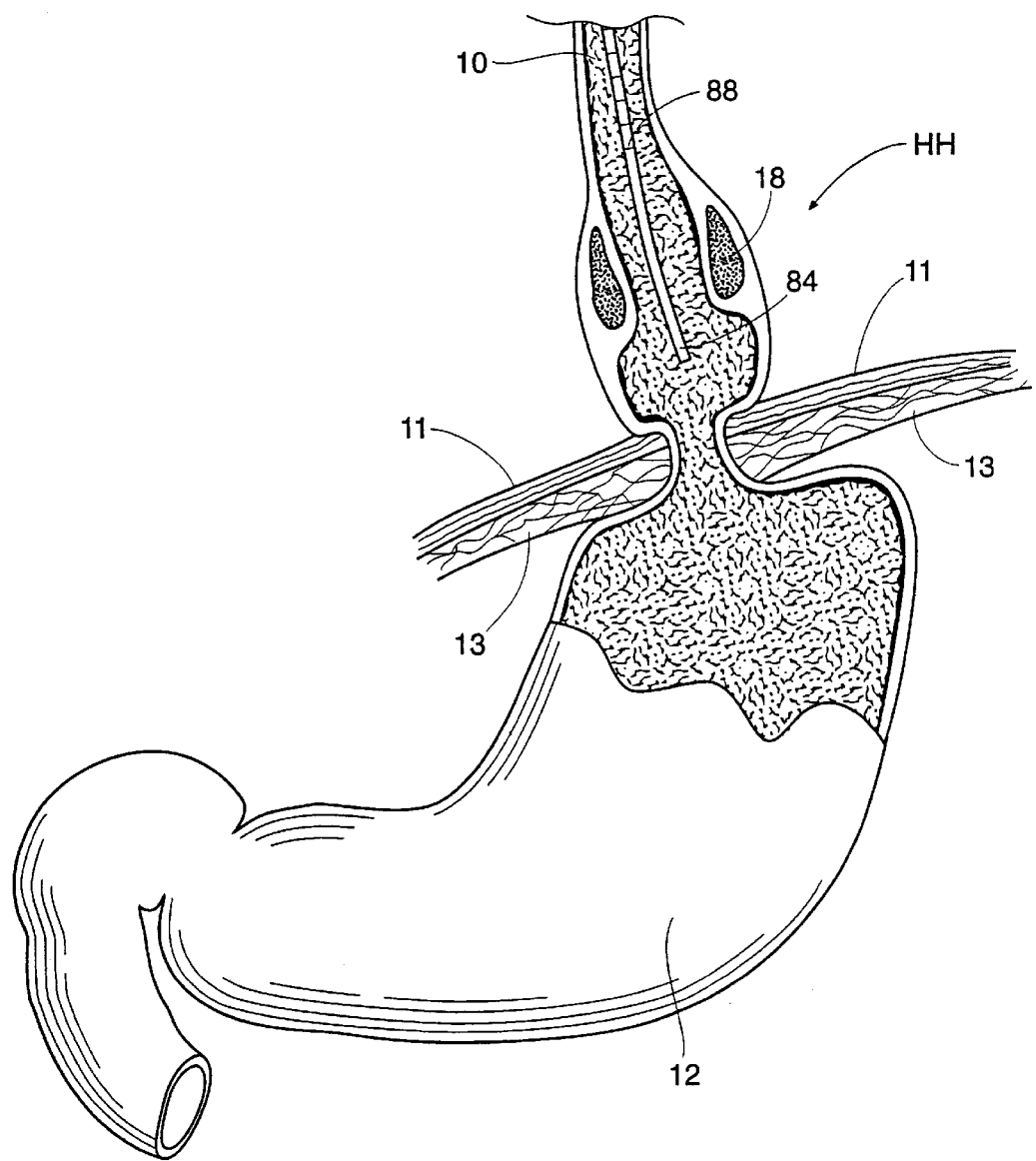
FIG. 9 is a side view of the a hiatal hernia, showing the lower esophageal sphincter and a portion of a stomach penetrating through the diaphragm.

In a person suffering from a hiatal hernia HH, the lower esophageal sphincter 18 and the upper part of the stomach 20 protrudes through the esophageal hiatus 15, passing through to the top side of the diaphragm 11 and into the chest cavity, as is shown illustratively in FIG. 1C and in cross section on FIG. 9.

It should be noted that the views of the esophagus and stomach shown in FIGS. 1, 1A–E and elsewhere in the drawings are not intended to be strictly accurate in an anatomic sense. The drawings show the esophagus, crura, diaphragm and stomach in somewhat illustrative form to demonstrate the features of the invention.

II. Systems for Sphincters or Adjoining Tissue Regions

A. System Overview

Figure 2:
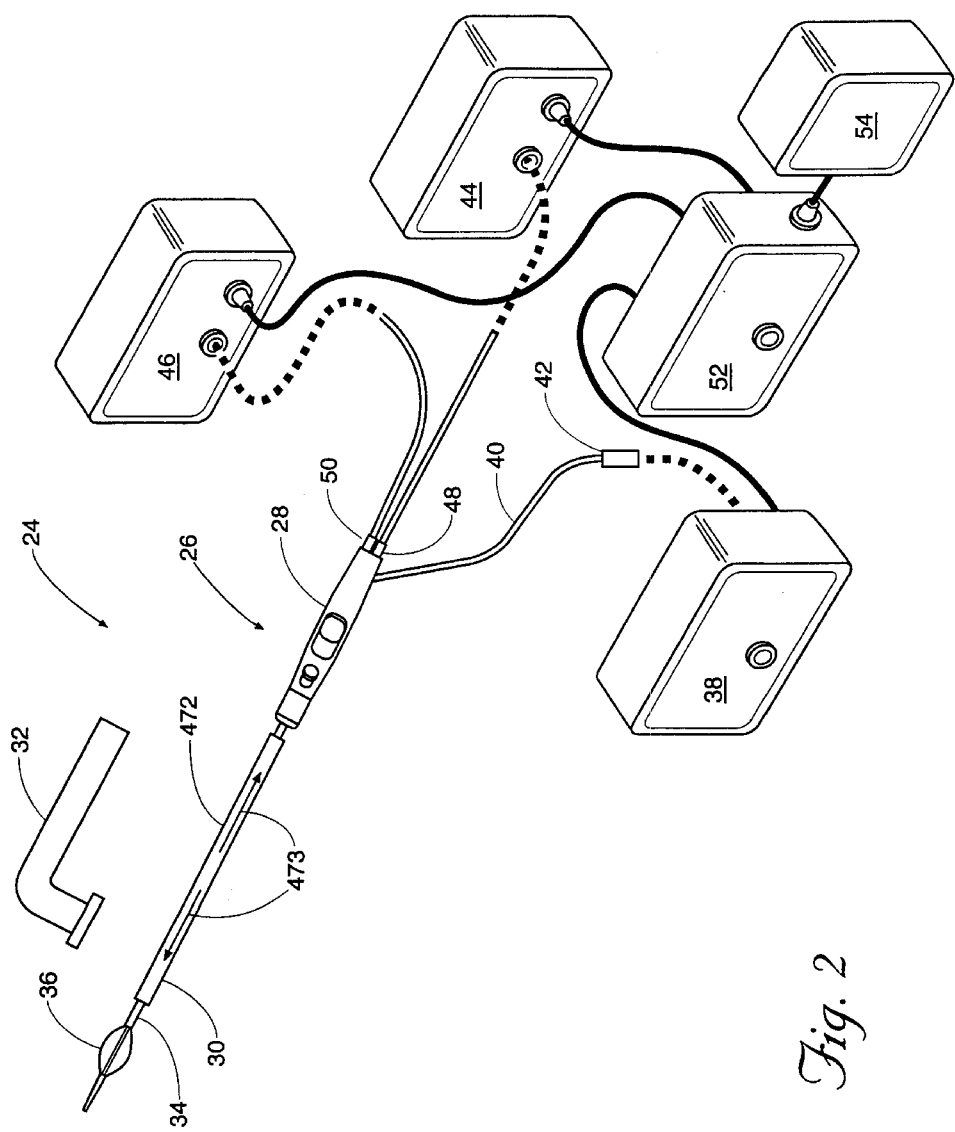
FIG. 2 is a diagrammatic view of a system for treating a hiatal hernia region, which embodies features of the invention.

FIG. 2 shows a system 24 for treating hiatal hernias. The system 24 may also be use to treat dysfunction of the lower esophageal sphincter 18 and/or the adjoining cardia 20 of the stomach 12, with or without treatment of a hiatal hernia.

The system 24 includes a treatment device 26. The device 26 includes a handle 28 made, e.g., from molded plastic. The handle 28 carries a flexible catheter tube 30. The catheter tube 30 can be constructed, for example, using standard flexible, medical grade plastic materials, like vinyl, nylon, poly(ethylene), ionomer, poly(urethane), poly(amide), and poly(ethylene terephthalate). The handle 28 is sized to be conveniently held by a physician, to introduce the catheter tube 30 into the esophagus 10. The details of using the treatment device 28 will be described later.

The handle 28 and the catheter tube 30 can form an integrated construction intended for a single use and subsequent disposal as a unit. Alternatively, the handle 28 can comprise a nondisposable component intended for multiple uses. In this arrangement, the catheter tube 30, and components carried at the end of the catheter tube 30 (as will be described), comprise a disposable assembly, which the physician releasably connects to the handle 28 at time of use and disconnects and discards after use. The catheter tube 30 can, for example, include a male plug connector that couples to a female plug receptacle on the handle 28.

The catheter tube 30 may be passed through the patient's mouth and pharynx, and into the esophagus 10, with or without the use of a guide wire. The system 24 may include an esophageal introducer 32, which aids in the deployment of the catheter tube 30 into the esophagus 10 through the mouth and throat of a patient.

The catheter tube 30 has a distal end 34, which carries an operative element 36. The catheter tube 30 can carry a protection sheath 472 (see FIG. 2) for the operative element 36. The sheath 472 slides along the catheter tube 30 (as indicated by arrows 473 in FIG. 2) between a forward position enclosing the operative element 36 and a rearward position free of the operative element 36. When in the forward position, the sheath 472 prevents contact between tissue and the operative element 36, thereby aiding in the deployment and removal of the operative element 36 through the patient's mouth and pharynx. When in the rearward position, the sheath 472 frees the operative element 36 for use.

With the operative element 36 freed for use, the herniated portion of the stomach is retracted downward into its normal location below the diaphragm. This may be accomplished in a number of ways. For example, hooks or other tissue-grabbing devices may be deployed from the catheter tube 30 to grasp the herniated esophagus and push the tissue below the diaphragm. Vacuum may also be applied to pull the tissue down onto the operative element 36. Alternatively, the stomach can be insufflated, or a large balloon can be inflated in the stomach to pull the hernia section downward, to a position below the diaphragm.

The operative element 36 applies energy in a selective fashion through the wall of the esophagus and into the crura 13 outside the esophageal wall. Energy is delivered to the crura 13 to cause shrinkage and/or a reduction in compliance, to thereby retain the previously herniated section below the diaphragm. Energy may also be applied to the esophageal wall itself, if desired.

The applied energy preferably creates one or more lesions, or a prescribed pattern of lesions, within the crura 13 below the mucosal surface of the esophagus 10 and spaced from the lower esophageal sphincter 18. The lesions are formed in the crura 13 in a manner that preserves and protects the mucosal surface of the esophagus 10 and the lower esophageal sphincter 18 against thermal damage.

It has been discovered that natural healing of the lesions in the crura 13 leads to a physical tightening of the crura 13. When the lower esophageal sphincter 18 in a person experiencing a hiatal hernia is returned back to its normal position below the diaphragm 11 and within the crura 13, the subsequent formation of lesions and the tightening of the crura 13 about the lower esophageal sphincter 18 holds the repositioned lower esophageal sphincter 18 in place, thereby treating or repairing the hiatal hernia.

The operative element 36, or another operative element separately deployed, can also apply energy in a selective fashion to the lower esophageal sphincter 18 itself, or to the cardia 20, or both. The applied energy creates one or more lesions, or a prescribed pattern of lesions, within the lower esophageal sphincter 18 or cardia 20 below the mucosal surface of the esophagus 10, in a manner that also preserves and protects the mucosal surface of the esophagus 10 against thermal damage. The natural healing of the lesions in the lower esophageal sphincter 18 or cardia 20 also leads to a physical tightening of these regions, as well. Further details of the treatment of the lower esophageal sphincter 18 or cardia 20, which can be used in association with treatment of the crura 13, are disclosed in copending U.S. patent application Ser. No. 09/304,737, filed May 4, 1999, and entitled "Systems and Methods for Treating the Cardia of the Stomach and Adjoining Tissue Regions of the Esophagus," which is incorporated herein by reference.

In this arrangement, the system 24 includes a generator 38 to supply the treatment energy. In the illustrated embodiment, the generator 38 supplies radio frequency energy, e.g., having a frequency in the range of about 400 kHz to about 10 mHz. Of course, other forms of energy can be applied, e.g., coherent or incoherent light; heated or cooled fluid; resistive heating; microwave; ultrasound; a tissue ablation fluid; or cryogenic fluid.

A cable 40 extending from the proximal end of the handle 28 terminates with an electrical connector 42. The cable 40 is electrically coupled to the operative element 36, e.g., by wires that extend through the interior of the handle 28 and catheter tube 30. The connector 42 plugs into the generator 38, to convey the generated energy to the operative element 36.

The system 24 also includes certain auxiliary processing equipment. In the illustrated embodiment, the processing equipment comprises an external fluid delivery apparatus 44 and an external aspirating apparatus 46.

The catheter tube 30 includes one or more interior lumens (not shown) that terminate in fittings 48 and 50, located on the handle 28. One fitting 40 connects to the fluid delivery apparatus 44, to convey processing fluid for discharge by or near the operative element 36. The other fitting 50 connects to the aspirating apparatus 46, to convey aspirated material from or near from the operative element 36 for discharge.

The system 24 also includes a controller 52. The controller 52, which preferably includes a central processing unit (CPU), is linked to the generator 38, the fluid delivery apparatus 44, and the aspirating apparatus 46. Alternatively, the aspirating apparatus 46 can comprise a conventional vacuum source typically present in a physician's suite, which operates continuously, independent of the controller 52.

The controller 52 governs the power levels, cycles, and duration that the radio frequency energy is distributed to the operative element 36, to achieve and maintain power levels appropriate to achieve the desired treatment objectives. In tandem, the controller 52 also governs the delivery of processing fluid and, if desired, the removal of aspirated material.

The controller 52 includes an input/output (I/O) device 54. The I/O device 54 allows the physician to input control and processing variables, to enable the controller to generate appropriate command signals. The I/O device 54 also receives real time processing feedback information from one or more sensors associated with the operative element (as will be described later), for processing by the controller 52, e.g., to govern the application of energy and the delivery of processing fluid. The I/O device 54 also includes a graphical user interface (GUI), to graphically present processing information to the physician for viewing or analysis. Further details regarding the GUI are found in copending U.S. patent application Ser. No. 09/305,123, filed May 4, 1999 and entitled "Graphical User Interface for Association with an Electrode Structure Deployed in Contact with a Tissue Region," which is incorporated herein by reference.

B. Operative Element

Figure 3:
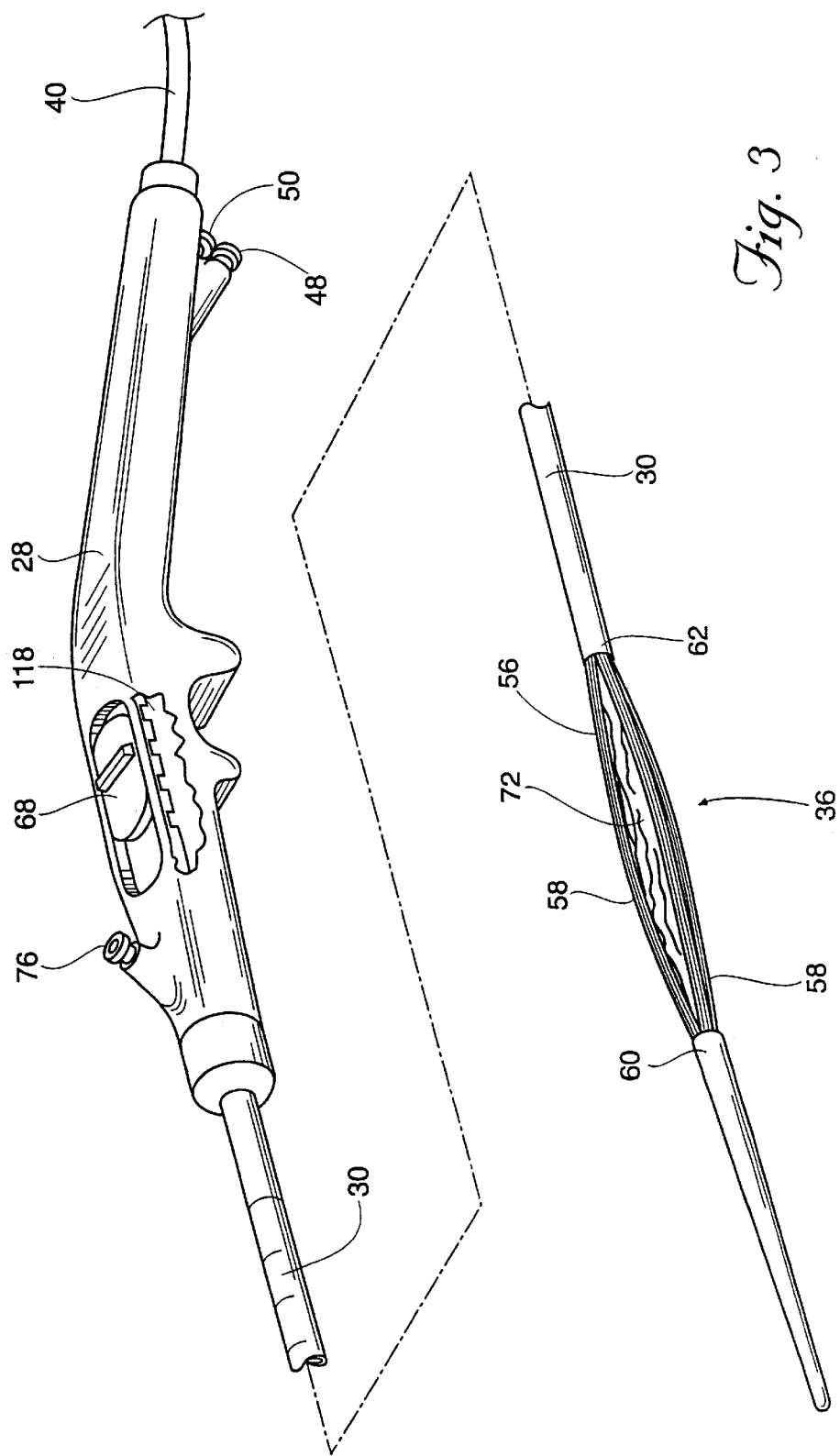
FIG. 3 is a perspective view, with portions broken away, of a device usable in association with the system shown in FIG. 2 having an operative element for contacting tissue shown in a collapsed condition.

The structure of the operative element 36 can vary. In the embodiment shown in FIGS. 3 to 7, the operative element 36 comprises a three-dimensional basket 56. The basket 56 includes one or more spines 58, and typically includes from four to eight spines 58, which are assembled together by a distal hub 60 and a proximal base 62. In FIG. 3, the spines 58 are equally circumferentially spaced apart in side-by-side pairs. Alternatively, the spines 58 can be arranged in singular, spaced apart relationship.

Each spine 58 preferably comprises a flexible tubular body made, e.g. from molded plastic, stainless steel, or nickel titanium alloy. The cross sectional shape of the spines 58 can vary, possessing, e.g., a circular, elliptical, square, or rectilinear shape. In the illustrated embodiment, the spines 58 possess a rectilinear shape to resist twisting.

Figure 4:
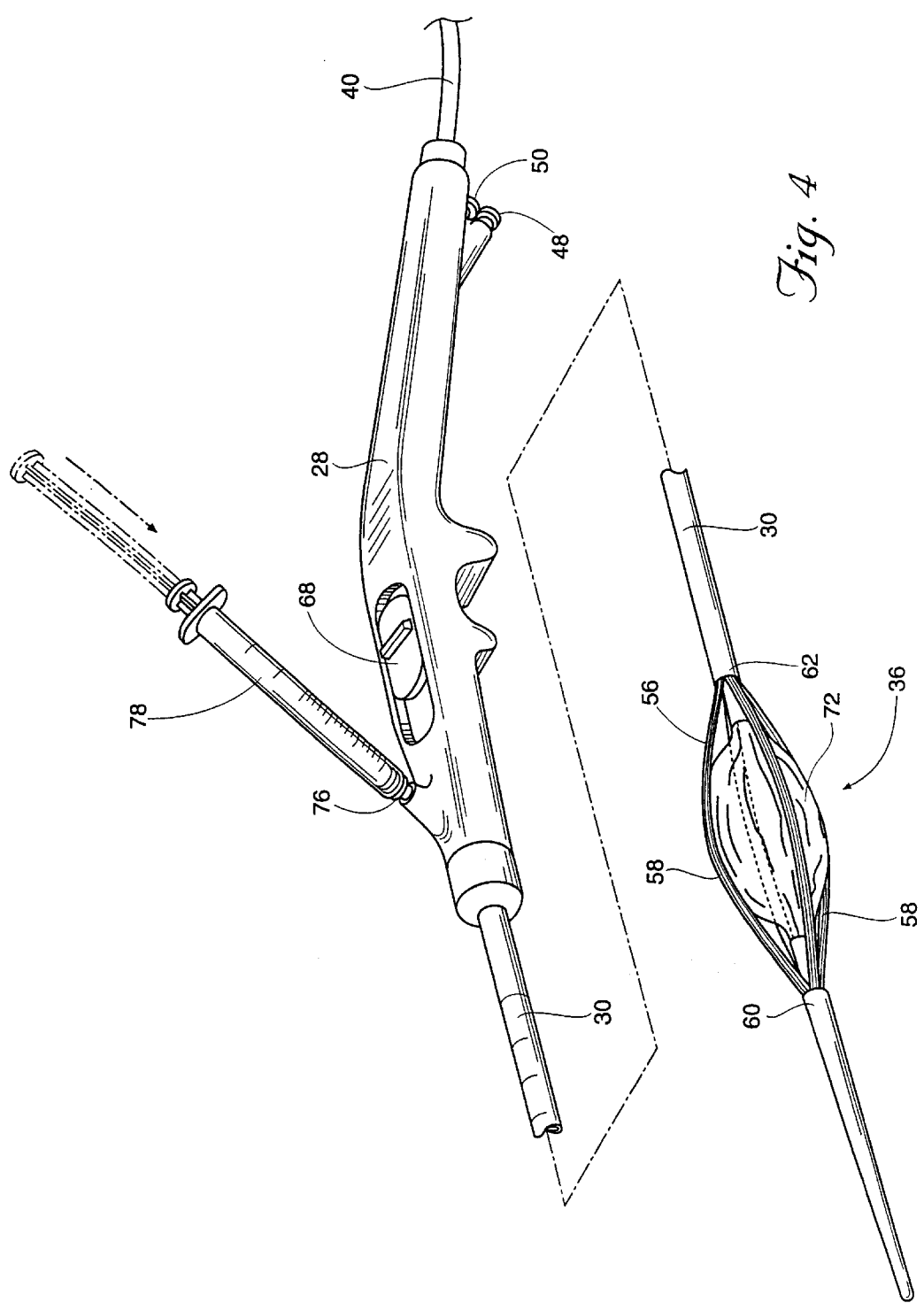
FIG. 4 is a perspective view, with portions broken away, of the device shown in FIG. 3, with the operative element shown in an expanded condition.
Figure 5:
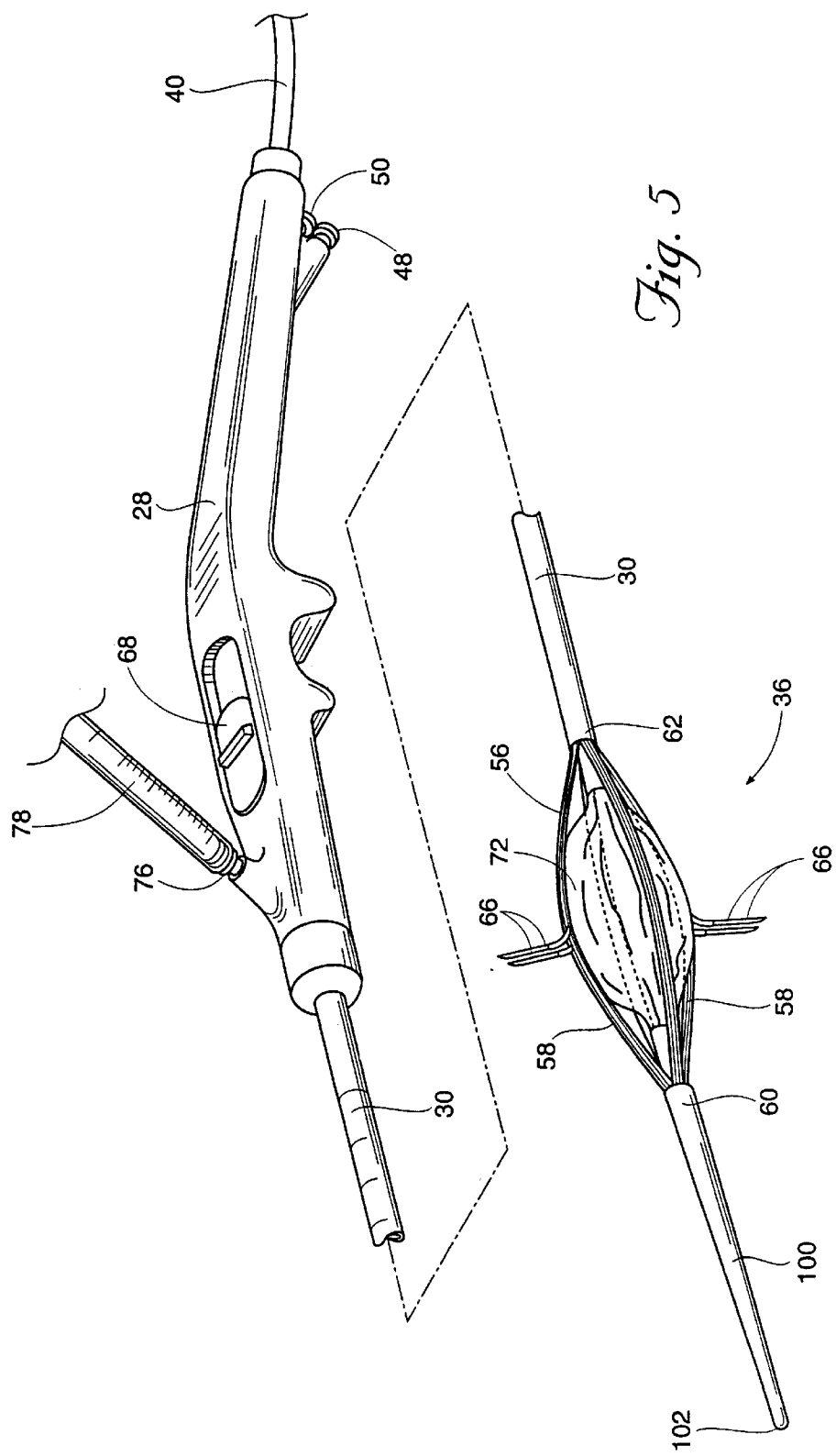
FIG. 5 is a perspective view, with portions broken away, of the device shown in FIG. 3, with the operative element shown in an expanded condition and the electrodes extended for use.
Figure 6:
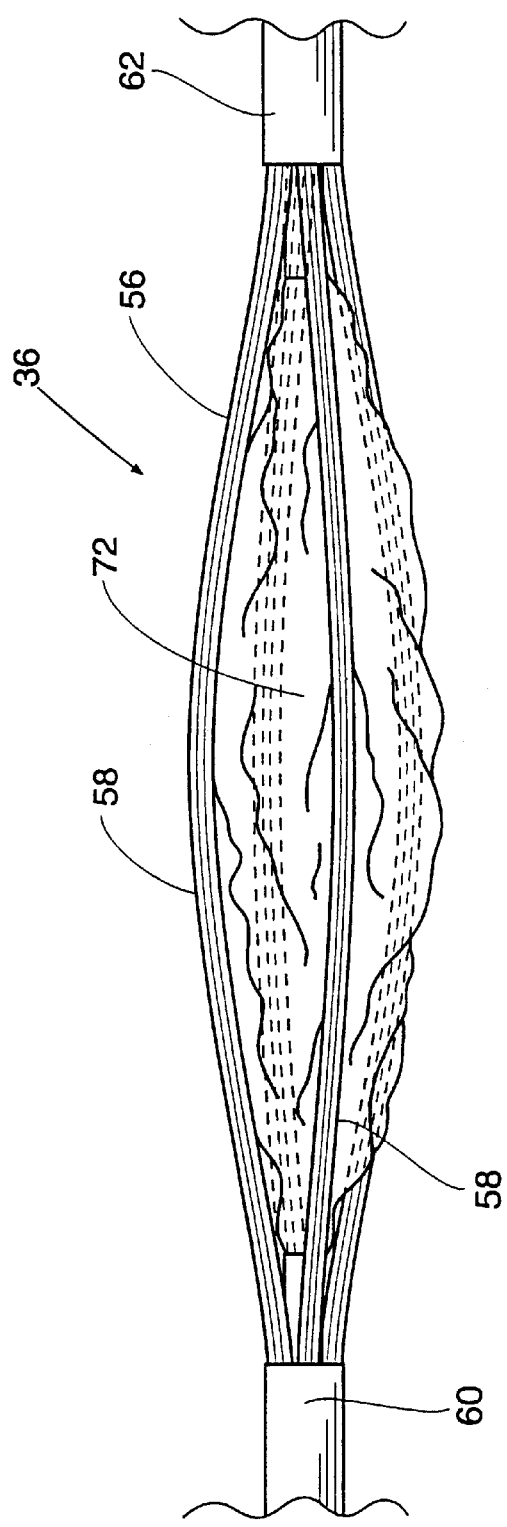
FIG. 6 is an enlarged side view of the operative element when collapsed, as also shown in FIG. 3.
Figure 7:
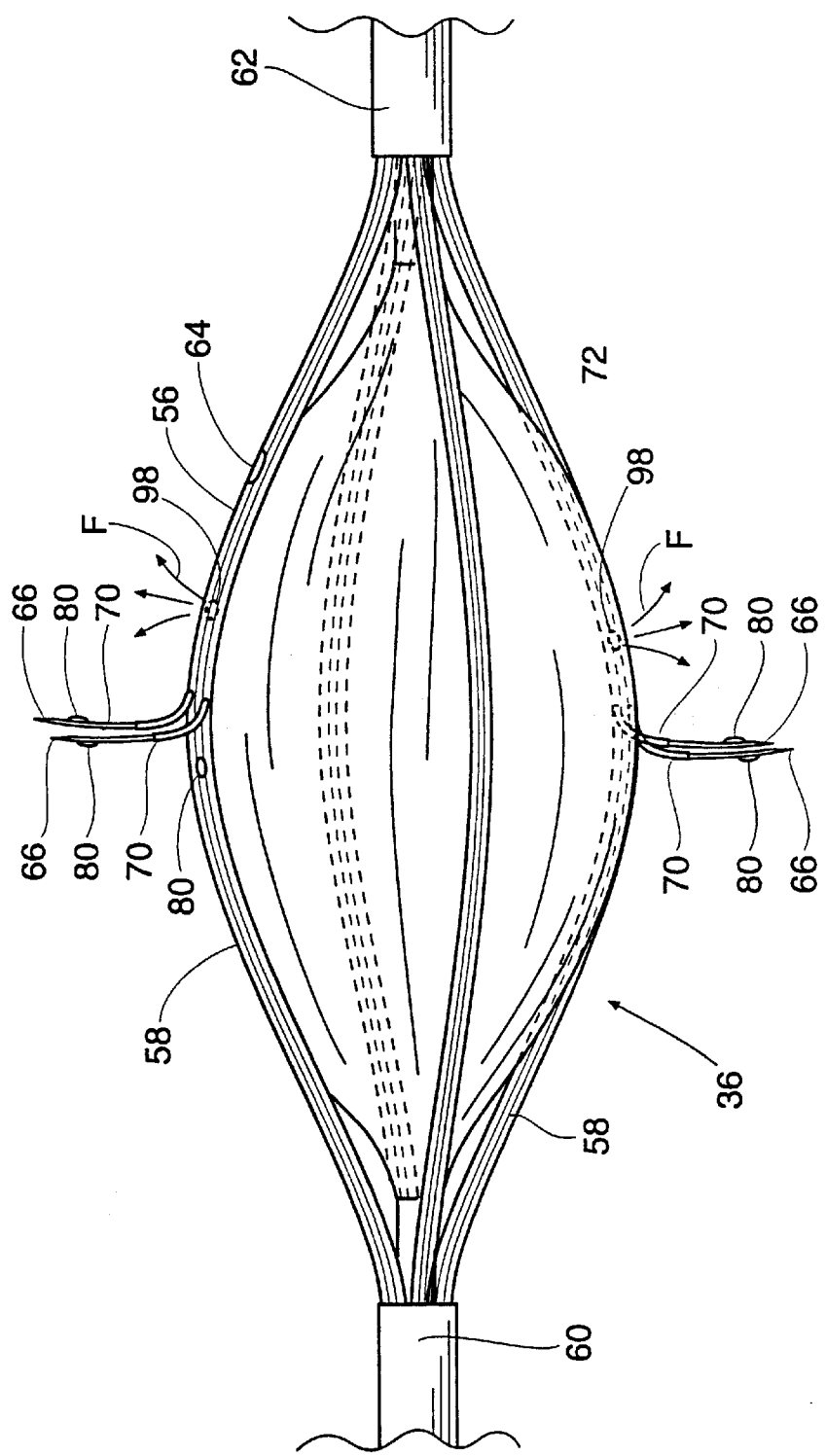
FIG. 7 is an enlarged side view of the operative element when expanded and with the electrodes extended for use, as also shown in FIG. 5.

Each spine 58 carries an electrode 66 (see FIGS. 5 and 7). In the illustrated embodiment, each electrode 66 is carried within the tubular spine 58 for sliding movement. Each electrode 66 slides from a retracted position, withdrawn in the spine 58 (shown in FIGS. 3, 4, and 6), and an extended position, extending outward from the spine 58 (see FIGS. 5 and 7) through a hole in the spine 58 and sleeve 64. If the spines 58 are arranged in singular, spaced apart relationship, single electrodes 66 can be deployed from each spine 58.

A push-pull lever 68 on the handle 28 is coupled by one or more interior wires to the sliding electrodes 66. The lever 68 controls movement electrodes between the retracted position (by pulling rearward on the lever 68) and the extended position (by pushing forward on the lever 68).

The electrodes 66 can be formed from various energy transmitting materials. In the illustrated embodiment, the electrodes 66 are formed from nickel titanium. The electrodes 66 can also be formed from stainless steel, e.g., 304 stainless steel, or a combination of nickel titanium for the distal portion and stainless steel for the proximal portion. The nickel titanium alloy performs best in a curved region of the electrode 66, due to its super-elastic properties. The use of stainless steel in the proximal portion can reduce cost, by minimizing the amount of nickel titanium alloy required. The different materials may be joined, e.g., by crimping, swaging, soldering, welding, or adhesive bonding, which provide electrical continuity between or among the various materials. One or both of the materials may be flattened to an oval geometry and keyed together to prevent mutual twisting. In a preferred embodiment, the proximal portion comprises an oval stainless steel tube, into which a distal curved region having a round cross section and made of nickel titanium is slipped and keyed to prevent mutual twisting.

The electrodes 66 can be formed in various sizes and shapes. The electrodes 66 can possess, e.g., a circular cross sectional shape or a cross section that provides increased resistance to twisting or bending as the electrodes penetrate tissue. For example, the electrodes 66 can possess a rectangular cross section, or an elliptical cross section. Other cross sections, e.g., conical or pyramidal, can also be used to resist twisting. The surface of the electrode 66 can, e.g., be smooth, or textured, or concave, or convex.

The electrodes 66 have sufficient distal sharpness and strength to penetrate a desired depth into the crura 13. For penetration into the crura 13, the desired depth can range from about 9 mm to 11 mm, and preferably is about 10 mm.

To further facilitate penetration and anchoring in the crura 13, each electrode 66 is preferably biased with a bend. The electrodes 66 can be bent in either an antegrade or retrograde direction over an arc of ninety degrees or less. The bend provides a secure anchorage in tissue. Retraction of the electrodes 66 into the spines 58 overcomes the bias and straightens the electrode 66 when not in use. In the illustrated embodiment (see FIG. 5), each electrode 66 is normally biased with an antegrade bend (i.e., bending toward the proximal base 62 of the basket 56). Alternatively, each electrode 66 can be normally biased toward an opposite retrograde bend (i.e., bending toward the distal hub 60 of the basket 58).

The depth of electrode penetration can also be controlled, e.g., through mechanical linkages or ratches associated with the push-pull lever 68 on the handle 28, or by use of a stop located on the electrode 66, to prevent puncture through the targeted tissue region. An electrical measurement can also be made to determine penetration of an electrode 66 in tissue. For example, by applying electrical energy at a frequency (e.g., 5 kHz) less than that applied for lesion formation, impedance of a given electrode 66 can be assessed. The magnitude of the impedance varies with the existence of tissue penetration and the depth of tissue penetration. A high impedance value indicates the lack of tissue penetration. The impedance value is lowered to the extent the electrode penetrates the tissue.

An endoscopic or ultrasonic visualization function may also be incorporated into the operative element 36, or be used in conjunction with it, to aid in positioning by observing and directing electrode deployment.

As FIG. 7 shows, an electrical insulating material 70 is coated about the proximal end of each electrode 66. The electrical insulating material 70 can comprise, e.g., a Polyethylene Terephthalate (PET) material, or a polyimide or polyamide material. For deployment in the crura 13, the length of the electrical insulating material 70 should extend over a substantial portion of the proximate portion of each electrode 66, to individually insulate each electrode 66. For deployment in the crura 13, each electrode 66 preferably presents a conductive (i.e., non-insulated) length of about 2 mm to about 15 mm, to provide an exposed surface area at the distal end of each electrode 66 of preferably about 3 mm$^2$ to about 20 mm$^2$. When the distal end of the electrode 66 penetrates the crura 13, the material 70 insulates the mucosal surface of the esophagus 10 and the muscle of the lower esophageal sphincter 18 from direct exposure to the radio frequency energy. Thermal damage to these tissue masses overlaying the crura 13 is thereby avoided. The mucosal surface of the esophagus 10 can also be actively cooled during application of radio frequency energy, to further protect the mucosal surface from thermal damage. If desired, though, the extent of the insulating material 70 can be varied to apply radio frequency energy to the muscular tissue of the LES and/or esophagus, to thereby treat these regions as well.

The ratio between exposed and insulated regions on the electrodes 66 affects the impedance of the electrodes 66 during use. Generally speaking, the larger the exposed region is compared to the insulated region, a lower impedance value can be expected, leading to a fewer incidences of power shut-offs due to high impedance.

Of course, a greater or lesser number of spines 58 and/or electrodes 66 can be present, and the geometric array of the spines 58 and electrodes 66 can vary.

In the embodiment shown in FIG. 3, an expandable structure 72 comprising a balloon is located within the basket 56. The balloon structure 72 can be made, e.g., from a Polyethylene Terephthalate (PET) material, or a polyamide (non-compliant) material, or a radiation cross-linked polyethylene (semi-compliant) material, or a latex material, or a silicone material, or a C-Flex (highly compliant) material. Non-compliant materials offer the advantages of a predictable size and pressure feedback when inflated in contact with tissue. Compliant materials offer the advantages of variable sizes and shape conformance to adjacent tissue geometries.

Alternatively, the operative element can include an expandable, three-dimensional, mechanical basket, with jointed spines that are pivotally carried between a distal hub and a proximal base, or an expandable, extruded basket structure. Further details of these alternative construction are found in copending U.S. patent application Ser. No. 09/304, 773 filed May 4, 1999 and entitled "Expandable Electrode Assemblies for Forming Lesions to Treat Dysfunction in Sphincters and Adjoining Tissue Regions," which is incorporated herein by reference.

The balloon structure 72 presents a normally, generally collapsed condition, as FIGS. 3 and 6 show. In this condition, the basket 56 is also normally collapsed about the balloon structure 72, presenting a low profile for deployment into the esophagus 10.

Figure 8:
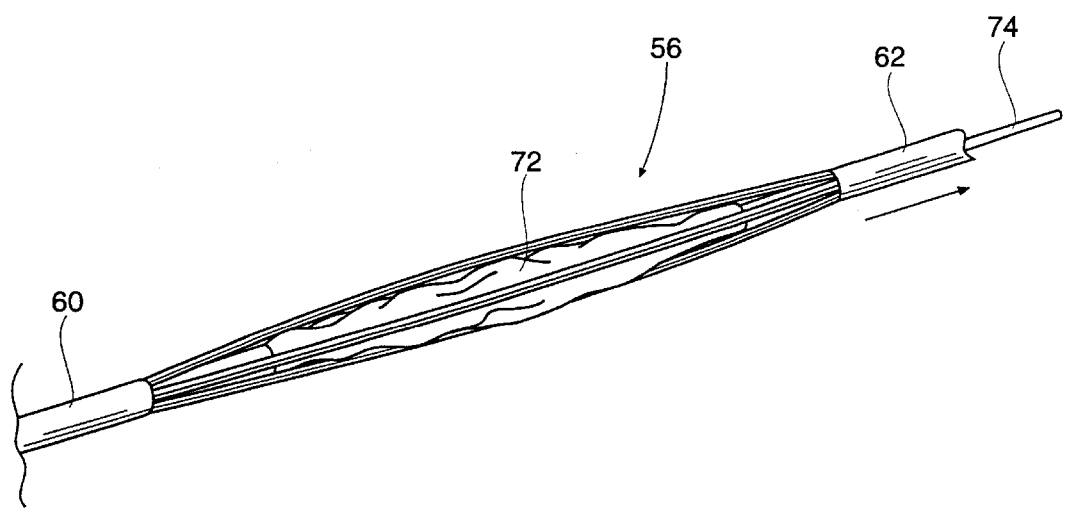
FIG. 8 is an enlarged perspective view of an embodiment of the operative element, when fully collapsed.

To aid in the collapse of the basket 56 (see FIG. 8), one end (hub 60 or base 62) of the basket 56 can be arranged to slide longitudinally relative to the other end of the basket 56, which is accordingly kept stationary. A stylet 74 attached to the slidable end of the basket 56 (which, in FIG. 8, is the base 62) is controlled, e.g., by a push-pull mechanism on the handle 28. The stylet 74, when pulled, serves to move the ends 58 and 60 of the basket 56 apart when the balloon structure 72 is collapsed. A full collapse of the basket 56 is thereby possible (as FIG. 8 shows) to minimize the overall profile of the basket 56 for passage through the esophagus 10. The push-pull mechanism can include a lock to hold the stylet 74 stationary, to maintain the basket 56 in the fully collapsed condition during deployment.

The catheter tube 30 includes an interior lumen, which communicates with the interior of the balloon structure 72. A fitting 76 (e.g., a syringe-activated check valve) is carried by the handle 28. The fitting 76 communicates with the lumen. The fitting 76 couples the lumen to a syringe 78 (see FIGS. 4 and 5). The syringe 78 injects fluid under pressure through the lumen into the balloon structure 72, causing its expansion.

Expansion of the balloon structure 72 urges the basket 56 to open and expand (as FIGS. 4, 5, and 7 show). The force exerted by the balloon structure 72, when expanded, is sufficient to exert an opening force upon the tissue surrounding the basket 56. Preferably, for deployment in the esophagus 10, the magnitude of the force exerted by the balloon structure 72 is between about 0.01 to 0.5 lbs. For deployment in the esophagus 10 in the region of the crura 13, the diameter of the balloon structure 72, when expanded, can be optimized at about 2 cm to 3 cm.

In the illustrated embodiment, the controller 52 can condition selected pairs of electrodes 66 to operate in a bipolar mode. In this mode, one of the electrodes comprises the transmitter and the other electrode comprises the return for the transmitted energy. The bipolar electrode pairs can comprise adjacent side-by-side electrodes 66 on a given spine, or electrodes 66 spaced more widely apart on different spines. Alternatively, the electrodes 66 can be conditioned to operate in a monopolar mode in association with an indifferent patch electrode (not shown), which serves as a common return for all electrodes 66. In the alternative arrangement, where electrodes 66 arranged in singular, spaced apart relation, the electrodes 66 can also be operated either in a bipolar or monopolar mode.

In the illustrated embodiment (see FIG. 7), each electrode 66 carries at least one temperature sensor 80. Each electrode can carry two temperature sensors 80, one to sense temperature conditions near the exposed distal end of the electrode 66, and the other to sense temperature conditions in the insulated material 70. Preferably, the second temperature sensor 80 is located on the corresponding spine 58, which rests against the mucosal surface of the esophagus 10 when the balloon structure 72 is inflated.

In use (see FIG. 9), the patient lies awake in an upright position. A visualization device 84 comprising, e.g., an endoscope carried at the end of a flexible catheter tube (or other suitable visualizing mechanism) is deployed to view the region of the lower esophageal sphincter 18 and the hiatal hernia HH. The catheter tube for the endoscope 84 includes measured markings 88 along its length. The markings 88 indicate the distance between a given location along the catheter tube and the endoscope 84. With the markings 88, the physician can gauge, in either relative or absolute terms, the distance between the patient's mouth and the endoscope 84 in the esophagus 10, and thereby gauge the location of the lower esophageal sphincter 18 and the hiatal hernia HH.

Figure 10:
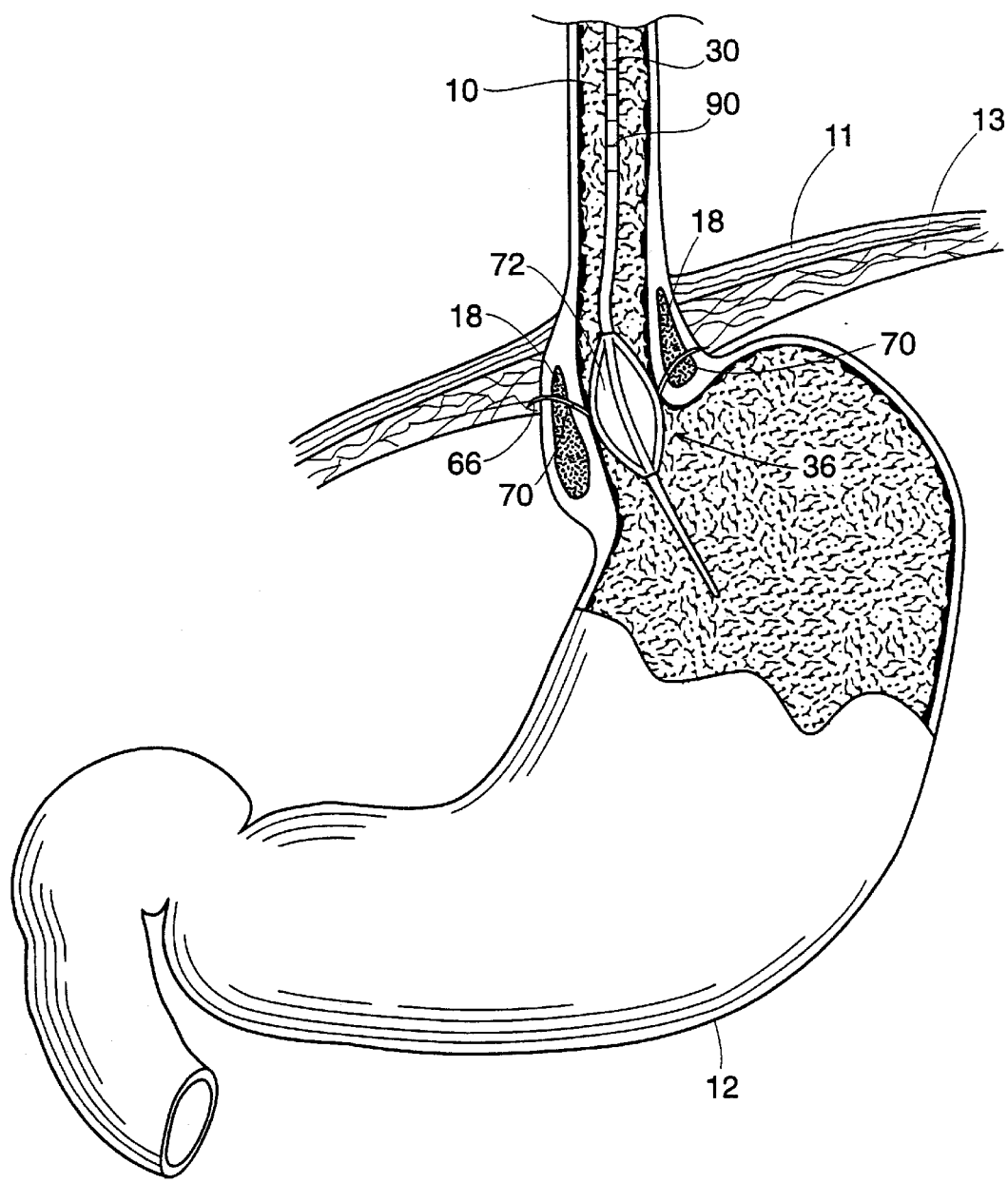
FIG. 10 is a side view of the deployment of the device shown in FIG. 3, after the lower esophageal sphincter has been returned to the region of the crura, as expanded into contact with mucosal tissue in the region of the lower esophageal sphincter, and with the electrodes deployed to apply radio frequency energy to create lesions in the crura.

The physician next takes steps to move the stomach downward, in order to move the lower esophageal sphincter 18 back below the diaphragm 11 into the region of the crura 13. The physician can, e.g., insert a tube through the patient's mouth into the stomach, and convey carbon dioxide gas into the stomach through the tube. The carbon dioxide gas distends the stomach to urge the stomach downward, thereby pulling the lower esophageal sphincter 18 through the diaphragm 11. The catheter tube may also incorporate mechanisms to deploy hooks or vacuum or a large balloon or insufflation by other means, to pull the lower esophageal sphincter 18 back to the region of the crura 13 (as FIG. 10 shows), thereby drawing the herniated tissue back below the diaphragm 11 before delivering energy. These functions can also be accomplished by a separate catheter or an endoscope.

The physician continues to visualizes the interior of the esophagus, to determine when the desired repositioning of the lower esophageal sphincter 18 has occurred.

When the lower esophageal sphincter 18 has been returned to the region of the crura 13 (see FIG. 10), the physician records the markings 88 on the endoscope catheter tube, which indicate the location of the lower esophageal sphincter 18. As FIG. 10 shows, the physician passes the catheter tube 30 carrying the operative element 36 through the esophagus 10. For the passage, the expandable balloon structure 72 is in its collapsed condition, and the electrodes 66 are in their retracted position. The physician can keep the endoscope 84 deployed for viewing the deployment of the operative element 36, either separately deployed in a side-by-side relationship with the catheter tube 30, or by deployment through a lumen in the catheter tube 30 or deployment of the structure 72 through a lumen in the endoscope 84 itself. If there is not enough space for side-by-side deployment of the endoscope 84, the physician deploys the endoscope 84 before and after deployment of the structure 72.

The catheter tube 30 includes measured markings 90 along its length. The measured markings 90 indicate the distance between a given location along the catheter tube 30 and the operative element 36. The markings 90 on the catheter tube 30 correspond in spacing and scale with the measured markings 88 along the endoscope catheter tube. The physician can thereby relate the markings 90 on the catheter tube 30 to gauge, in either relative or absolute terms, the location of the operative element 36 inside the esophagus 10. When the markings 90 indicate that the operative element 36 is at the desired location, i.e., at the repositioned lower esophageal sphincter 18, which is now adjoining the crura 13, the physician stops passage of the operative element 36. The operative element 36 is now located at the site targeted for treatment.

Once located at the targeted site, the physician operates the syringe 78 to convey fluid or air into the expandable balloon structure 72. The structure 72, and with it, the basket 56, expand, to make intimate contact with the mucosal surface of the esophagus 10. The expanded balloon structure 72 serves to temporarily dilate the lower esophageal sphincter 18, to remove some or all the folds normally present in the mucosal surface. The expanded balloon structure 72 also places the spines 58 in intimate contact with the mucosal surface.

The physician pushes forward on the lever 68 to move the electrodes 66 into their extended position (as FIG. 10 shows). The electrodes 66 pierce and pass through the mucosal tissue, through the lower esophageal sphincter 18, and into the crura 13.

The physician commands the controller 52 to apply radio frequency through one or more of the electrodes 66. The energy can be applied simultaneously or in any desired sequence. The energy ohmically heats the crura 13 adjacent to the electrodes 66. The controller 52 samples temperatures sensed by the sensors 80 to control the application of energy. When each electrode 66 in a given pair carries at least one temperature sensor 80, the controller 52 can average the sensed temperature conditions or select the maximum temperature condition sensed for control purposes.

The controller 52 processes the sensed temperatures in a feedback loop to control the application of energy. The GUI can also display the sensed temperatures and the applied energy levels. Alternatively, the physician can manually control the energy levels based upon the temperature conditions displayed on the GUI.

Preferably, for a region of the crura 13, energy is applied to achieve tissue temperatures in the range of 55° C. to 95° C. In this way, lesions can be created below the mucosal surface. Typical energies range, e.g., between 100 and 1000 joules per electrode pair.

It is desirable that the lesions possess sufficient volume to evoke tissue healing processes accompanied by intervention of fibroblasts, myofibroblasts, macrophages, and other cells. The healing processes results in a contraction of tissue about the lesion, to decrease its volume or otherwise alter its biomechanical properties. The healing processes naturally tighten the tissue in the crura 13, to hold the repositioned lower esophageal sphincter 18 in place. A bipolar energy path between the electrodes 66 creates, for a given amount of energy, lesions of greater volume than is typically created in a monopolar fashion.

To create greater lesion density in a given targeted tissue area, it is also desirable to create a pattern of multiple lesions, e.g., in rings in the crura 13.

Various lesions patterns can be achieved. A preferred pattern comprises multiple rings of lesions, with 8 to 16 lesions per ring. The physician can create a given lesion pattern by expanding the balloon structure 72 and extending the electrodes 66 at the targeted treatment site, to form a first set of lesions. The physician then withdraws the electrodes 66, collapses the balloon structure 72, and rotates the catheter tube 30 by a desired amount. The physician then again expands the structure 72 and again extends the electrodes 66, to achieve a second set of lesions. The physician repeats this sequence until a desired ring of lesions is formed. Additional rings of lesions can be created by advancing the operative element axially, gauging the ring separation by the markings 90 on the catheter tube 30.

Other, more random or eccentric patterns of lesions can be formed to achieve the desired density of lesions within a given targeted site.

In treating the crura 13, the electrodes 66 are oriented to avoid contacting or penetrating the anterior and posterior vagus 17 (shown on FIGS. 1B and 1E), which lay between the lower esophageal sphincter 18 and the crura 13. If desired, prior to applying treatment energy, the operator can attempt nerve stimulation by delivery of low energy through one or more of the electrodes 66. If nerve stimulation occurs, the physician knows that the electrodes 66 are deployed into or in close association with either vagus nerve 17 and should be relocated.

The operative element 36 can be used in the manner described to treat the crura 13 in a single procedure. If desired, another operative element 36 can also be deployed during the same session or at a later session to treat either the cardia 20 or the lower esophageal sphincter 18 individually, to thereby provide a further tightening of these tissue regions.

In one embodiment, at least one spine 58 (and preferably all spines) includes an interior lumen 98 (see FIG. 7). The fluid delivery apparatus 44 conveys processing fluid F through the lumen 98 for discharge at the treatment site. The processing fluid F can comprise, e.g., saline or sterile water, to cool the mucosal suface while energy is being applied by the electrode 66 to ohmically heat muscle beneath the surface.

In this arrangement (see FIG. 5), the catheter tube 30 includes a distal tail 100, which extends beyond the hub 60 of the basket 56. An interior lumen 102 extends through the tail 100 and the interior of the balloon structure 72 to connect to the fitting 48. The aspirating apparatus 46 draws aspirated material and the processing fluid through this lumen 102 for discharge. This arrangement provides self-contained aspiration for the operative element 36. Other aspiration configurations can be used, as shown in copending U.S. patent application Ser. No. 09/304,784, filed May 4, 1999 and entitled "Actively Cooled Electrode Assemblies for Forming Lesions to Treat Dysfunction in Sphincters and Adjoining Tissue Regions," which is incorporated herein by reference.

A given electrode 66 deployed by an operative device can also be used to deliver drugs independent of or as an adjunct to lesion formation. In this arrangement, the electrode 66 includes an interior lumen (not shown). As before explained, a submucosal lesion can be formed by injecting an ablation chemical through the lumen, instead of or in combination with the application of ablation energy by the electrode. Any electrode 66 possessing the lumen can also be used to deliver drugs to the targeted tissue site.

For example, tissue growth factors, fibrosis inducers, fibroblast growth factors, or sclerosants can be injected through the electrode lumen, either without or as an adjunct to the application of energy to ablate the tissue. Tissue bulking can also be achieved by the injection of collagen, dermis, cadaver allograft material, or PTFE pellets through the electrode lumen. If desired, radio frequency energy can be applied to the injected bulking material to change its physical characteristics, e.g., to expand or harden the bulking material, to achieve a desired effect.

There are alternative methods of tightening the crura so as to retain the stomach below the diaphragm using a minimally-invasive catheter-based system, as just described. For example, a catheter-based system can be used to deploy sutures or staples through the wall of the esophagus or stomach into the crura, to thereby retain the stomach below the diaphragm.

Various features of the invention are set forth in the following claims.

We claim:

1. A method for treating hiatal hernia comprising the steps of locating the stomach in a proper intra-abdominal position below the diaphragm, introducing a catheter tube into a region of the esophagus adjoining the crura, and advancing a tissue penetrating element from the catheter tube through a wall of the esophagus and into contact with tissue in one or more crura, and tightening the one or more crura using the tissue penetrating element, to thereby retain the stomach in the proper intra-abdominal position.

2. A method according to claim 1 further comprising the step of applying energy to the contacted tissue through the tissue penetrating element to form a lesion.

3. A method according to claim 2 wherein radio frequency energy is applied.

4. A method according to claim 2 wherein the tissue penetration element ablates the contacted tissue.

5. A method according to claim 2 further comprising the step of delivering a tissue ablating agent through the tissue penetrating element.

6. A method according to claim 2 further comprising the step of delivering a tissue bulking agent through the tissue penetrating element.

7. A method according to claim 2 further comprising the step of delivering an agent comprising at least one of a tissue growth factor, fibrosis inducer, fibroblast growth factor, and sclerosants through the tissue penetrating element.

* * * * *